United States Patent
Pappas

(10) Patent No.: US 6,344,043 B1
(45) Date of Patent: Feb. 5, 2002

(54) ANTERIOR-POSTERIOR FEMORAL RESECTION GUIDE WITH SET OF DETACHABLE COLLETS

(76) Inventor: Michael J. Pappas, 8650 S. Ocean Blvd., Jensen Beach, FL (US) 34987

( * ) Notice: Subject to any disclaimer, the term of this patent is extended or adjusted under 35 U.S.C. 154(b) by 0 days.

(21) Appl. No.: 09/529,848

(22) PCT Filed: Nov. 18, 1998

(86) PCT No.: PCT/US98/24589

§ 371 Date: Apr. 19, 2000

§ 102(e) Date: Apr. 19, 2000

(87) PCT Pub. No.: WO99/25263

PCT Pub. Date: May 27, 1999

Related U.S. Application Data

(60) Provisional application No. 60/065,672, filed on Nov. 18, 1997.

(51) Int. Cl.[7] ............................................. A61B 17/17
(52) U.S. Cl. ............................. 606/96; 606/79; 606/80; 606/88
(58) Field of Search ............................. 606/80, 88, 89, 606/96, 86

(56) References Cited

U.S. PATENT DOCUMENTS

| | | |
|---|---|---|
| 4,718,413 A | 1/1988 | Johnson |
| 4,721,104 A | 1/1988 | Kaufman et al. |
| 4,738,253 A | 4/1988 | Buechel et al. |
| 4,738,254 A | 4/1988 | Buechal et al. |
| 4,759,350 A | 7/1988 | Dunn et al. |
| 4,791,919 A | 12/1988 | Elloy et al. |
| 4,892,093 A | 1/1990 | Zarnowski et al. |
| 5,053,037 A | 10/1991 | Lackey |
| 5,100,408 A | 3/1992 | Lackey |
| 5,282,803 A | 2/1994 | Lackey |
| 5,486,178 A | 1/1996 | Hodge |
| 5,486,855 A | 1/1996 | Bouraly et al. |
| 5,514,140 A | 5/1996 | Lackey |
| 5,562,675 A | 10/1996 | McNulty et al. |
| 5,662,656 A | 9/1997 | White |
| 5,735,856 A | 4/1998 | McCue et al. |
| 5,735,904 A | 4/1998 | Pappas |
| 5,741,264 A | 4/1998 | Cipolletti |
| 5,810,829 A | 9/1998 | Elliott et al. |

*Primary Examiner*—David O. Reip
(74) *Attorney, Agent, or Firm*—Anthony J. Casella; Gerald E. Hespos

(57) ABSTRACT

A set of instruments (10) is provided for use in the preparation of a natural bone of a condylar joint for receiving prosthetic components both in primary and revision surgery. To illustrate the invention and use thereof, reference is made to the preparation of a natural femur (F) in a knee joint. The set of instruments (10) includes an anterior-posterior femoral resection guide (12) having a guide aperture (36) formed therethrough, and a set of collets (14; 16; 18A; 18B) formed to detachably mount to the guide aperture (36). The set of collets (14; 16; 18A; 18B) includes a drill guide (14), a reamer sleeve (16), and a plurality of different size reamer bushings (18A; 18B). Accordingly, the drill guide (14) can be mounted to the anterior-posterior femoral resection guide (12) to provide guidance in the drilling of a channel (87) into the distal end of a femur (F), and, alternatively, the combination of the reamer sleeve (16) and the reamer bushings (18A; 18B) can be used to provide guidance in reaming a channel into the distal end of a femur (F). As an additional feature, a tibial template (98) is also provided which can be cooperatively used with the reamer sleeve (16) and reamer bushings (18A; 18B) to prepare a channel into a natural tibia (T).

11 Claims, 5 Drawing Sheets

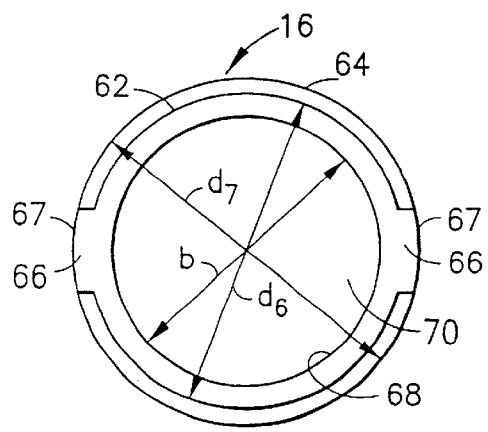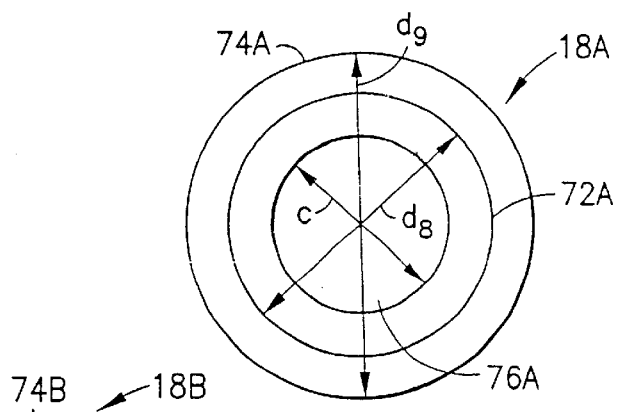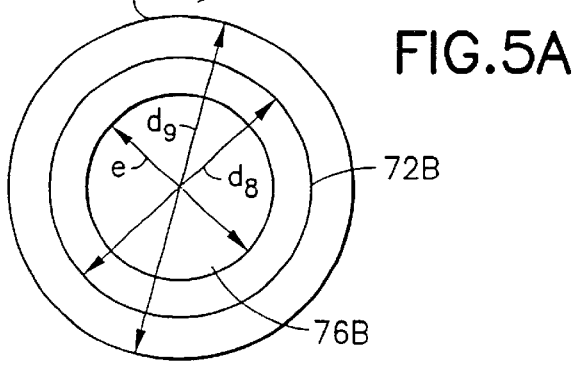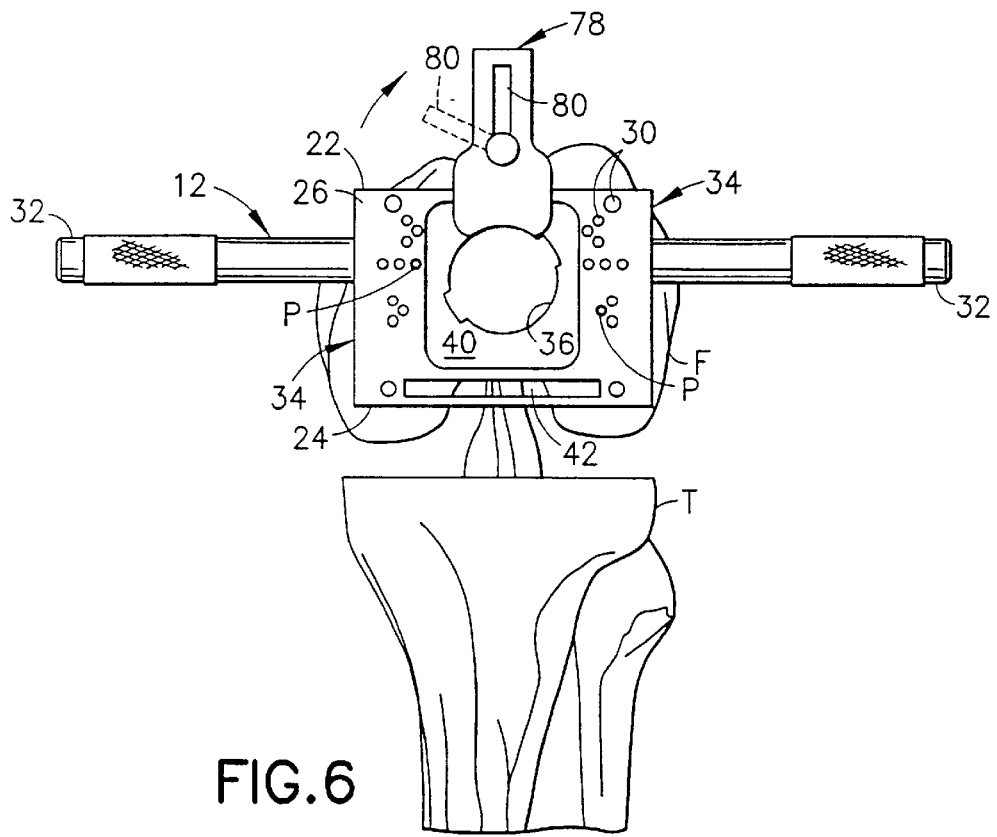

ANTERIOR-POSTERIOR FEMORAL RESECTION GUIDE WITH SET OF DETACHABLE COLLETS

This application claims priority on U.S. Provisional Appl. 60/065,672, filed Nov. 18, 1997.

BACKGROUND OF THE INVENTION

1. Field of the Invention

This invention relates to surgical instruments and, more particularly, to instruments for preparing natural bone for receiving prosthetic components.

2. Description of the Prior Art

Many surgical techniques are known in the prior art for preparing the natural bones of a knee joint for receiving prosthetic components. Although the surgical techniques vary, the techniques provide a tibia and a femur with the resected surfaces shaped for receiving prosthetic components. In particular, the techniques vary in philosophical approaches to knee preparation, wherein the techniques vary by selecting either the tibia or femur to be initially prepared, applying different sequences in the order of surgical steps, and designating different resected surfaces as reference planes for preparing other resected surfaces. Additionally, surgical techniques vary with the type of prosthetic implantation being performed: primary implantation (first-time implantation) or revision implantation (replacement of failed or worn prosthetic components). It should be noted that there are rare instances where patients have seriously degenerated bones in the knee joint and require the application of the revision technique for primary implantation.

One technique for the primary implantation of prosthetic components in a knee is disclosed in a brochure entitled "ULTRA™ Tricompartmental Knee System", containing a surgical procedure prepared by Frederick F. Buechel, M. D., and published by Biomedical Engineering Trust, 1998. Additionally, a technique used in revision implantation of a knee prosthesis is disclosed in a brochure entitled "Buechel-Pappas™ Modular Knee Revision System with Rebar® Screws", containing a surgical procedure prepared by Frederick F. Buechel, M. D., and published by Biomedical Engineering Trust, January, 1998. The two aforementioned brochures are incorporated by reference herein for the description of these surgical techniques.

Due to the differences in techniques between primary and revision surgery, different surgical instruments are used with respect to each technique. Moreover, revision surgery requires a much greater number of instruments than primary surgery. To reduce the necessary number of instruments needed to be maintained in a operating room, efforts have been made in the prior art to combine multiple surgical functions into a single instrument or set of instruments. For example, the aforementioned surgical techniques both may utilize the surgical instruments, including the anterior-posterior femoral resection guide, described in U.S. Pat. No. 5,735,904 which issued on Apr. 7, 1998 to the inventor herein, entitled "SPACER FOR ESTABLISHING PROSTHETIC GAP AND LIGAMENTOUS TENSION". The disclosure of U.S. Pat. No. 5,735,904 is incorporated by reference herein. As disclosed in U.S. Pat. No. 5,735,904, the anterior-posterior femoral resection guide is provided with a fixed drill guide used in forming a pilot hole in the femur. As such, the anterior-posterior femoral resection guide efficiently serves two specific functions in addition to acting as a reference element in evaluating spacing between the tibia and the femur (as disclosed in U.S. Pat. No. 5,735,904): guidance for anterior and posterior resections of the femur; and guidance for drilling a pilot hole.

In revision surgery, a patient often requires the implantation of a stem into the femur to provide lateral stability to the prosthetic assembly in addition to the normal compressive loading applied thereto. The implantation of a stem, however, requires the formation of a channel in the femur through removal of bone. Typically, the channel is formed by first boring a 9 mm pilot hole into the distal end of the femur using a drill guide, such as that supported by the above-describe anterior-posterior femoral resection guide; removing the instrument supporting the pilot hole drill guide from the distal end of the femur; mounting a reaming guide; and sequentially using increasingly larger reamers to remove the soft inner bone of the femur and to eventually cut a cylindrical passage of predetermined length into the femoral endosteal cortex. In the prior art, a reamer guide or guides, separate from the drill guide and anterior-posterior femoral resection guide, are introduced to guide the reamers. However, the additional time and step of changing guides during surgery is undesired.

It is an object of the subject invention to provide a single set of instruments to prepare proper anterior and posterior femoral resections in primary surgery, as well as, revision surgery.

It is also an object of the subject invention to provide an anterior-posterior femoral resection guide with a set of detachable collets formed for guiding a drill, as well as, guiding various sized reamers.

SUMMARY OF THE INVENTION

The aforementioned objects are met by a set of instruments which includes an anterior-posterior femoral resection guide, and a set of collets formed to detachably mount onto the resection guide. Accordingly, the same set of instruments advantageously serves several functions both in primary and revision surgery.

The anterior-posterior femoral resection guide specifically has a generally rectangular body with planar anterior and posterior resection guide surfaces each formed to guide a prior art reciprocating saw in resecting anterior and posterior portions of a natural femur, respectively. Additionally, the resection guide has a guide aperture formed therethrough for interchangeably receiving the collets.

The set of collets includes a unitary tubular drill guide, preferably formed with a 9 mm inner passage, and a subset of reaming components, which, in turn, includes a unitary tubular reamer sleeve and a plurality of tubular reamer bushings. The reamer sleeve is formed to telescopically receive and accommodate each of the reamer bushings, and the reamer bushings are each shaped and formed to define a different inner diameter for accommodating a different sized reamer.

The drill guide and the reamer sleeve are formed to be directly detachably mounted to the guide aperture of the resection guide. It is preferred that a bayonet locking arrangement be utilized for achieving the direct detachable mounting. Particularly, the aperture of the resection guide is formed with a groove extending radially therefrom inset into the body of the resection guide, with two diametrically opposed recesses being formed in the body of the resection guide above the groove to create open passages thereto. Correspondingly, the drill guide and the reamer sleeve are each formed with diametrically opposed protruding ears dimensioned to pass through the recesses and slide into the groove upon being twisted.

For use during primary implantation, the resection guide of the subject invention is aligned and mounted onto the distal end of a femur. A yoke may be provided to align the anterior resection guide surface with the anterior femoral cortex. To align the resection guide, the resection guide is centered between the femoral epicondyles, and, preferably, the anterior resection guide surface is made level with the anterior femoral cortex. Once aligned, the resection guide is affixed to the femur using two or more bone pins. The drill guide is then mounted to the guide aperture, and a 9 mm channel, called a pilot hole, is bored into the femur using any prior art drilling instrument. An intramedullary rod is inserted through the drill guide and into the pilot hole. The yoke, if used, and the bone pins are then removed, and the instruments and techniques of U.S. Pat. No. 5,735,904 are preferably utilized to establish proper ligamentous tension between the femur and the tibia. After the proper ligamentous tension has been established, the femoral resection guide is once again rigidly fixed to the femur with the bone pins, and a reciprocating saw is used to perform anterior and posterior resections of the femur using the anterior and posterior resection guide surfaces, respectively.

For use during revision surgery, the resection guide of the subject invention is aligned relative to the distal end of the femur as described above with primary surgery, with the anterior resection guide surface being preferably level with the anterior femoral cortex, and the resection guide body being centered between the epicondyles of the femur. After the resection guide body is properly aligned and fixed to the femur using bone pins, the drill guide is mounted to the guide aperture, and a 9 mm pilot hole is drilled into the femur. Where a femoral stabilizing stem is required, the drill guide is removed and the reamer sleeve is attached to the guide aperture. Thereafter, a 10 mm reamer bushing is telescopically slipped into the reamer sleeve and a similar sized reamer is introduced to accordingly ream the pilot hole to 10 mm. Increasingly larger diameter reamer bushings and reamers are sequentially introduced to incrementally increase the diameter of the channel being formed in the femur. The surgeon completes the reaming process upon forming a cylindrical channel of predetermined length into the femoral endosteal cortex. A blunt-tipped reamer, having the same diameter as the final reamer, is then passed through the reamer bushing and into the reamed passage to act as an intramedullary rod. Subsequently, the yoke and bone pins are removed and, if necessary, the ligamentous tension is inspected. Also, the resection guide may be fixed to the femur to provide guidance for any necessary anterior and posterior resections.

As an additional feature, the reamer sleeve and reamer bushings can advantageously be used in cooperation with a tibial template to provide guidance in the reaming of a channel into the tibia.

These and other features of the invention will be better understood through a study of the following detailed description and accompanying drawings.

BRIEF DESCRIPTION OF THE DRAWINGS

FIG. 4 is a bottom view of the reamer sleeve.

FIGS. 5A and 5B are respectively bottom views of two different reamer bushings.

FIG. 6 is a perspective view of the anterior-posterior femoral resection guide fixed to the distal end of a femur.

DETAILED DESCRIPTION OF THE INVENTION

Figure 1:
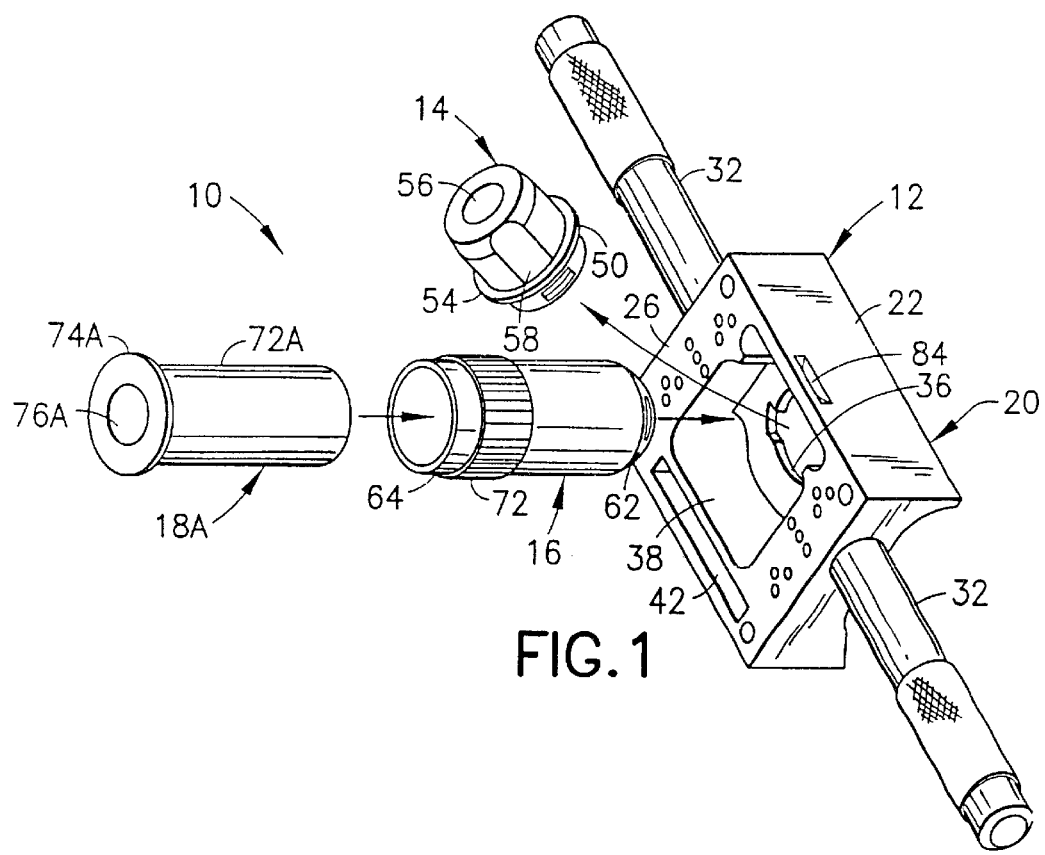
FIG. 1 is a perspective view of the subject invention.

FIGS. 1–11 generally depict a set of instruments 10 for use in preparing a natural femur F for receiving a prosthetic component. The set of instruments 10 includes an anterior-posterior femoral resection guide 12 and detachable collets. The detachable collets comprises a drill guide 14 and a subset of reamer components which includes, in turn, a reamer sleeve 16 and a plurality of reamer bushings 18A, 18B.

The anterior-posterior femoral resection guide 12 is formed with a general rectangular guide body 20 which defines a planar anterior resection guide surface 22 and a planar posterior resection guide surface 24. The guide body 20 also defines a relatively planar front face 26 and a rear face 28. As shown most clearly in FIG. 9, it is preferred that the rear face 28 be concave to maximize the possibility that the anterior and posterior resection guide surfaces 22 and 24 will be closer to the femur F than the rear face 28 in use. Consequently, the amount of gap between the anterior and posterior resection guide surfaces 22 and 24 and the femur F will be minimized, thereby improving the efficacy in the guidance of a reciprocating saw, as described below.

A plurality of bone pin apertures 30 are formed to extend between the front face 26 and the rear face 28 of the guide body 20. The bone pin apertures 30 are disposed at various locations about the front face 26 to increase the likelihood that a bone pin can be passed through the guide body 20 into engagement with relatively healthy bone stock of the femur F. In certain cases, severe deterioration of the femur F reduces the number of locations where a bone pin can be impacted into and held in a stable manner. To facilitate handling of the anterior-posterior femoral resection guide 12, handles 32 extend from side surfaces 34 of the guide body 20.

A guide aperture 36 is defined to extend through the guide body 20. As shown in FIG. 1, the guide body 20 is formed with a recess 38 extending into the front face 26. A recessed inner surface 40 is defined by the recess 38 about the guide aperture 36. Although not shown, the guide body 20 can be formed without the recess 38, with the guide aperture 36 extending through the entire guide body 20 to have an end coextensive with the front face 26. The guide body 20 is also preferably formed with a slot 42 to cooperate with an instrument in determining the proper spacing between a prepared tibia and the femur F in a prosthetic implantation operation.

Figure 2:
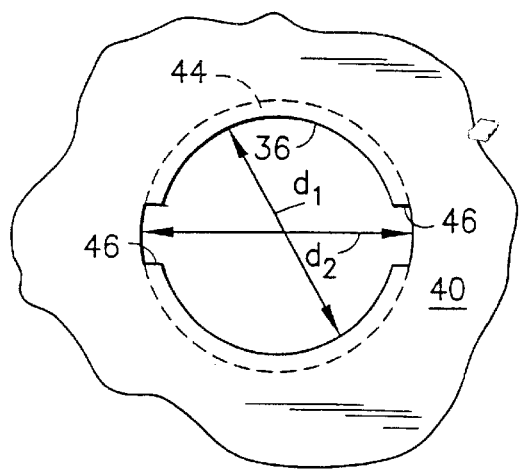
FIG. 2 is an enlarged view of the guide aperture formed in the anterior-posterior femoral resection guide.
Figure 2A:
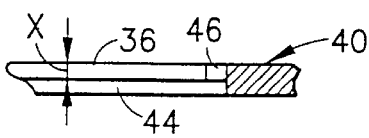
FIG. 2A is a partial cross-sectional view of the guide aperture.

The drill guide 14 and the reamer sleeve 16 are formed to directly detachably mount to the guide aperture 36. It is preferred that a bayonet locking arrangement be used to achieve such direct detachable mounting. In particular, with reference to FIGS. 2 and 2A, a groove 44 extends radially from the guide aperture 36, with the groove 44 being inset below the inner surface 40 a distance "X". Two diametrically opposed recesses 46 are formed through the inner surface 40 to communicate with the groove 44. As shown in FIG. 2, the guide aperture 36 defines a diameter "$d_1$", whereas, the groove 44 defines a diameter "$d_2$" which is greater than the diameter "$d_1$".

Figure 3:
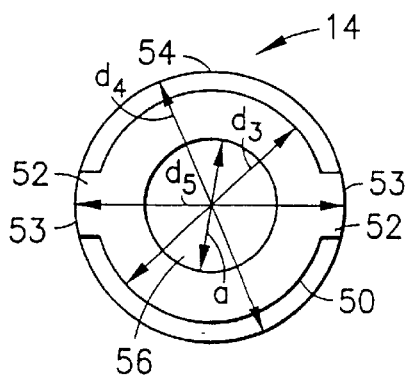
FIG. 3 is a bottom view of the drill guide.
Figure 3A:
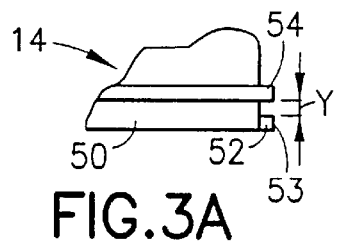
FIG. 3A is partial side view of the drill guide.

Correspondingly, as shown in FIG. 3, the drill guide 14 is generally tubular and formed with an annular base portion 50 from which two ears 52 extend in opposing radial directions. A flange 54 extends about the entire circumference of the drill guide 14 at a location adjacent to the annular base portion 50. The annular base portion 50 defines an outer diameter "$d_3$" which is slightly smaller than the diameter "$d_1$", whereas, the flange 54 defines an outer diameter "$d_4$" which is greater than the diameter "$d_1$". The ears 52 are dimensioned and located to simultaneously pass through the recesses 46 formed about the guide aperture 36. Preferably, outer surfaces 53 of the ears 52 define arc segments having a diameter "$d_5$" which is equal to or slightly smaller than the diameter "$d_2$". In this manner, the outer surfaces 53 are formed to bear against the groove 44 with the drill guide 14 being mounted to the guide aperture 36, as described below. Additionally, the ears 52 are spaced from the flange 54 a distance "Y", which is preferably equal to or slightly greater than the distance "X". In this manner, the ears 52 and the flange 54 bear against the groove 44 and the inner surface 40, respectively, also with the drill guide 14 being mounted to the guide aperture 36.

The drill guide 14 can be attached to the guide body 20 of the anterior-posterior femoral resection guide 12 by passing the ears 52 through the recesses 46 and turning the drill guide 14 to seat the ears 52 in the groove 44 below the inner surface 40. The flange 54 acts as a stop against excessive insertion of the drill guide 14 into the guide aperture 36. To detach the drill guide 14, the aforementioned operation is reversed, with the drill guide 14 being turned, and the ears 52 caused to pass through the recesses 46.

The drill guide 14 is also formed with an inner passage 56 through the entire length thereof defining a diameter "a". The diameter "a" is selected to allow passage therethrough of a drill bit, and preferably, a 9 mm drill bit. Thus, the diameter "a" is preferably nominally 9 mm. The drill guide 14 may also be formed with indentations 58 about the circumference thereof to facilitate handling of the drill guide 14.

The reamer sleeve 16 is generally tubular and formed with a base end 62 which defines an outer diameter "$d_6$". A main body 64 extends from the base end 62 and defines an outer diameter "$d_7$". Two ears 66 extend from the base end 62 in radially opposed directions. In like manner to the drill guide 14, the diameter "$d_6$" is formed to be slightly smaller than the diameter "$d_1$", the diameter "$d_7$" is formed to be greater than the diameter "$d_1$", and the ears 66 are formed and located to simultaneously pass through the recesses 46 formed about the guide aperture 36. Also, the ears 66 have outer surfaces 67 which preferably define arc segments having the diameter "$d_5$", and the ears 66 are spaced from the main body 64 the distance "Y". Accordingly, the reamer sleeve 16 can be easily attached and detached directly to the guide aperture 36 in the same manner as the drill guide 14, with the main body 64 acting as a stop against excessive insertion of the reamer sleeve 16 into the guide aperture 36.

The reamer sleeve 16 is also formed with an inner surface 68 which defines a channel 70 having a diameter "b". To facilitate handling of the reamer sleeve 16, a roughened or knurled surface 72 can be provided for enhanced gripping by a user of the device.

A plurality of the reamer bushings 18A, 18B is utilized with the invention. FIGS. 5A and 5B show by example first and second reamer bushings 18A and 18B, respectively. Although only two of the reamer bushings 18A, 18B are shown, any number of the reamer bushings 18A, 18B can be used with the invention. With reference to FIG. 5A, the first reamer bushing 18A has a generally tubular body 72A and protruding rim 74A formed at one end thereof. The body 72A defines an outer diameter "$d_8$", whereas, the rim 74A defines an outer diameter "$d_9$". Similarly, the second reamer bushing 18B is formed with a generally tubular body 72B, also defining the outer diameter "$d_8$", and a protruding rim 74B, also defining the outer diameter "$d_9$". For each of the reamer bushings 18A, 18B, the diameter "$d_8$" is selected to be slightly smaller than the diameter "b" of the reamer sleeve 16, meanwhile, the diameter "$d_9$" for each of the reamer bushings 18A, 18B is selected to be slightly greater than the diameter "b". In this manner, each of the reamer sleeves 18A, 18B can have the respective body 72A, 72B be telescopically slid into the channel 70 of the reamer sleeve 16, with the respective rim 74A, 74B, acting as a stop. As a result, with the reamer sleeve 16 being mounted to the guide aperture 36, the reamer bushings 18A, 18B can be indirectly detachably mounted to the anterior-posterior femoral guide 12.

Each of the reamers sleeve 18A, 18B is also formed to define a generally cylindrical inner passage 76A, 76B, respectively, which extends the full length thereof. For each of the reamers sleeve 18A, 18B, the respective inner passage 76A, 76B defines a different diameter. As shown in FIG. 5A, the inner passage 76A of the first reamer bushing 18A defines a diameter "c", while the inner passage 76B of the second reamer bushing 18B defines a diameter "e". The diameter "c" is smaller than the diameter "e". As is readily apparent, the first reamer bushing 18A is able to accommodate and guide a different size reamer than the second reamer bushing 18B. In this manner, a set of the reamer bushings 18A, 18B is prepared wherein the diameter of each of the respective inner passages 76A, 76B is different to provide a surgeon a full complement of reamer guides. Preferably, the inner passages will incrementally increase from reamer bushing to reamer bushing by 1 mm increments, and the smallest reamer bushing has an inner passage diameter of nominally 10 mm.

A yoke 78 may be used with the anterior-posterior femoral resection guide 12 to ensure proper alignment relative to the femur F. The yoke 78 is formed with a pivoting lock 80 having a detent 82 which is selectively rotated in and out of engagement with a groove 84 formed in the guide body 20 of the anterior-posterior femoral resection guide 12. The yoke 78 is also formed with a guide rod 86 which is shaped to be coplanar with the anterior resection guide surface 22 with the yoke 78 being mounted to the guide body 20.

Figure 7:
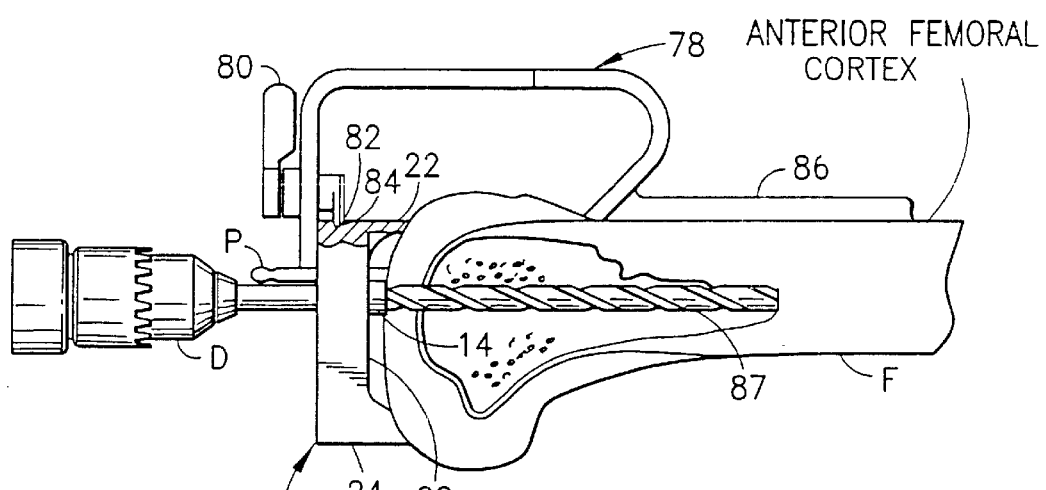
FIG. 7 is a side view, shown partially in cross section, of a drill being guided by the drill guide in forming a pilot hole into the distal end of the femur.
Figure 8:
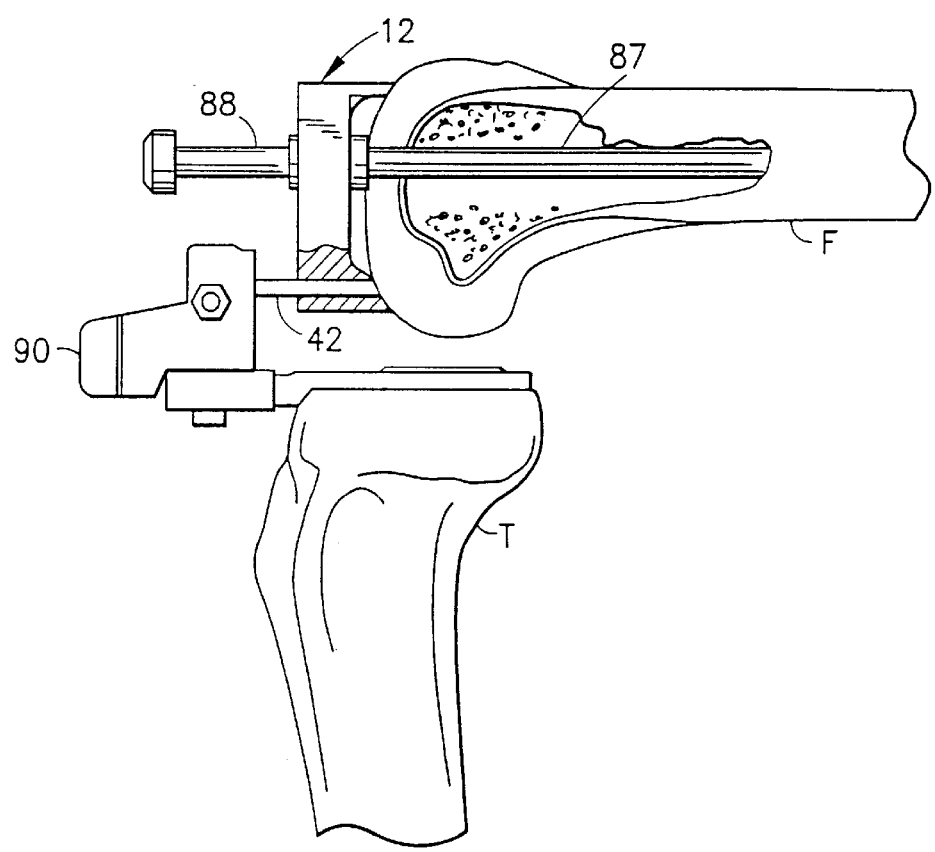
FIG. 8 is a side view, shown partially in cross section, of the anterior-posterior femoral resection guide being supported by an intramedullary rod and in cooperative use with the device of U.S. Pat. No. 5,735,904 for establishing proper ligamentous tension.
Figure 9:
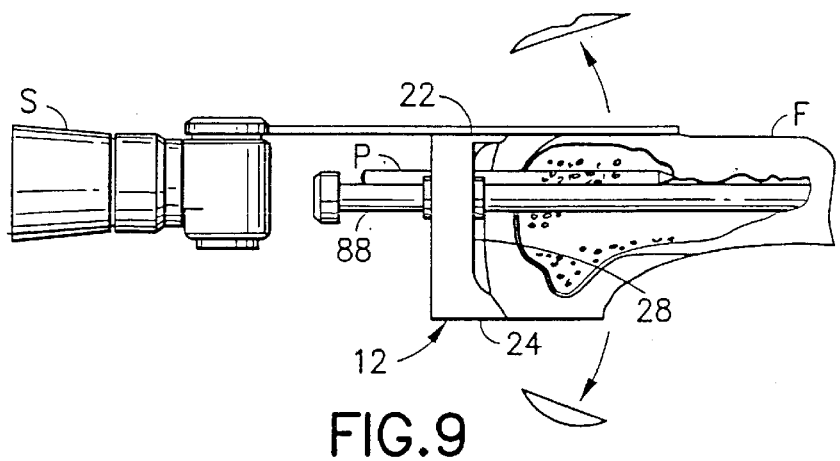
FIG. 9 is a side view, shown partially in cross section, of the anterior-posterior femoral resection guide in use in guiding a reciprocating saw in resecting anterior and posterior portions of the femur.

Consequently, as most clearly shown in FIG. 7, the yoke 78 can be used to ensure that the anterior resection guide surface 22 is made level with the anterior femoral cortex when mounting the anterior-posterior femoral resection guide 12 to the femur F. In this manner, as shown in FIG. 9, anterior portions of the condyles of the femur F can be resected without incising any portion of the anterior femoral cortex.

To illustrate use of the subject invention, FIGS. 6–9 depict several steps of a primary surgical implantation of a knee prosthesis. In the method contemplated herein, tibia T has a proximal portion resected prior to preparing the femur F. Once the tibia T is resected, attention is turned to the femur F, and the anterior-posterior resection guide 12 is mounted to a distal end of the femur F. To mount the anterior-posterior femoral resection guide 12 to the distal end of the femur F, the anterior-posterior femoral resection guide 12 is first aligned to be centered between the epicondyles of the femur F, and the yoke 78 (already being mounted to the guide body 20) is preferably used to level the anterior resection guide surface 22 with the anterior femoral cortex. After achieving proper alignment, the anterior-posterior femoral resection guide 12 is fixed to the femur F by bone pins P. As shown in FIG. 6, it is preferred at least two of the bone pins P are used, with the bone pins P being located on both sides of the guide aperture 36 to prevent rotation of the anterior-posterior femoral resection guide 12. After fixing the guide 12 to the femur F, the drill guide 14 is mounted into the guide aperture 36 and, as shown in FIG. 7, a drill D is introduced to form a channel 87, called a pilot hole, of predetermined length into the femur F. Thereafter, the drill D, the yoke 78 and the bone pins P are removed, and an intramedullary rod 88 is inserted through the drill guide 14 and into the pilot hole 87. An instrument 90, such as that disclosed in U.S. Pat. No. 5,735,904, may then be introduced, and used in combination with the slot 42, to ensure proper spacing between the femur F and the tibia T. Since the anterior-posterior femoral resection guide 12 is only supported by the intramedullary rod 88, the anterior-posterior femoral resection guide 12 can advantageously be rotated about the intramedullary rod 88 to ensure proper angular orientation is achieved in addition to the spacing.

After the proper spacing has been established, the bone pins P are used to fix the anterior-posterior femoral resection guide 12 to the femur F in a desired angular orientation. Referring to FIG. 9, a reciprocating saw S is subsequently introduced to resect anterior and posterior portions of the condyles of the femur F. As shown in FIG. 9, the anterior and posterior resection guide surfaces 22, 24 are used as guides.

Figure 10:
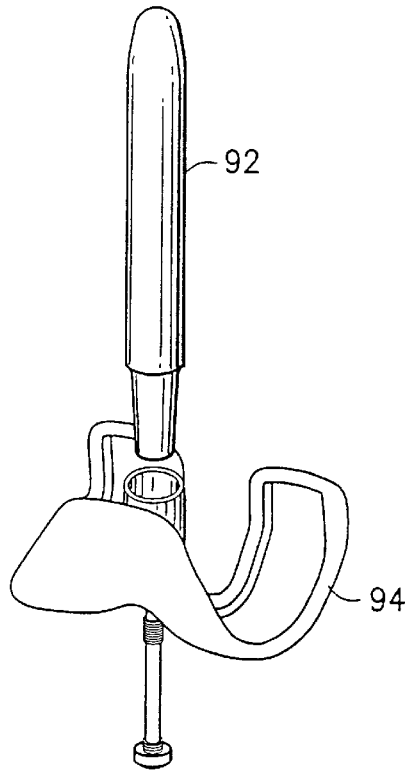
FIG. 10 is a perspective view of a typical femoral component having a stabilizing stem.
Figure 12:
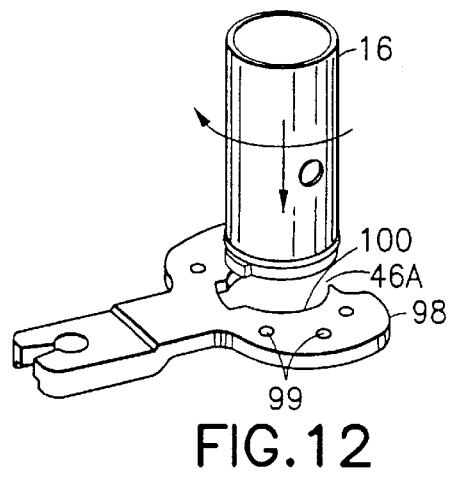
FIGS. 12–15 show a method for reaming a channel into a resected tibia using the reamer sleeve and reamer bushings of the subject invention.
Figure 11:
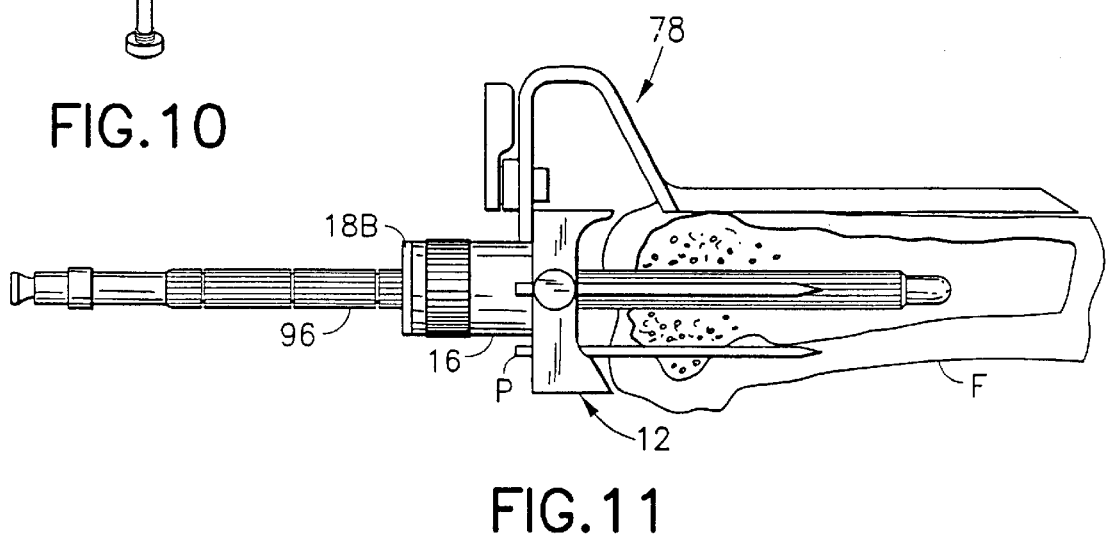
FIG. 11 is a side view, shown partially in cross section, of the anterior-posterior femoral resection guide being supported in a femur by a blunt-tipped reamer and bone pins.

In addition to the above-described steps of a primary implantation procedure, revision surgery often requires the additional step of preparing a channel into the femur F for receiving a stabilizing stem, such as that shown in FIG. 10 and designated with the reference numeral 92. The stabilizing stem 92 is rigidly anchored to a femoral prosthetic component 94 and can be formed with various lengths and diameters. Generally, the stabilizing stem 92 has a diameter greater than 9 mm and, thus, a larger channel must be formed in the femur F than the pilot hole 87. To prepare the femur F for receiving the stabilizing stem 92, an additional procedure of reaming the pilot hole 87 must be performed.

To illustrate an example of the use of the subject invention in revision surgery, the anterior-posterior femoral resection guide 12 is mounted to the femur F and the pilot hole 87 is prepared as described above with respect to primary surgery. The drill guide 14 is then removed and the reamer sleeve 16 is attached to the anterior-posterior femoral resection guide 12. The first reamer bushing 18A is telescopically slipped into the reamer sleeve 16. A reamer (not shown) having a diameter corresponding to the diameter of the inner passage 76A, is introduced and passed through the reamer bushing 18A to enlarge the pilot hole 87 to the corresponding reamer diameter. Increasingly larger reamer bushings and reamers are sequentially introduced to increase the diameter of the channel formed in the femur F. The reaming procedure continues until a generally cylindrical channel of predetermined length is formed in the femoral endosteal cortex. Thereafter, the final reamer is removed, and a blunt tipped reamer 96, having the same diameter as the final reamer, is passed through the reamer bushing (indicated with reference numeral 18B) and into the reamed passage in the femur F. The blunt tipped reamer 96 serves the same function as the intramedullary rod 88. At this point, the yoke 78 and the bone pins P can be removed, and any checking of spacing between the femur F and the tibia T can be performed, as well as, all needed anterior and posterior resecting.

Figure 13:
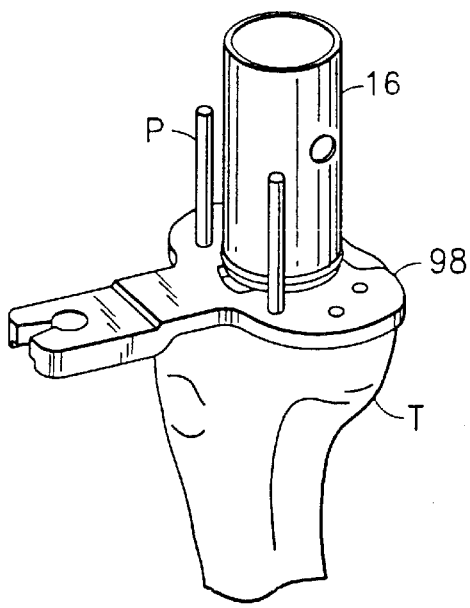
Figure 14:
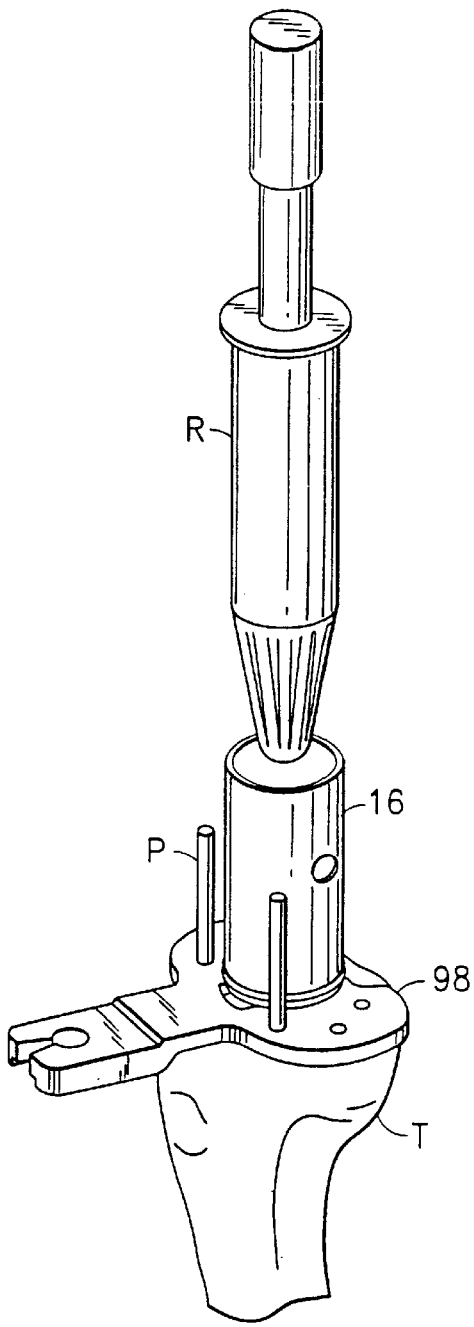
Figure 15:
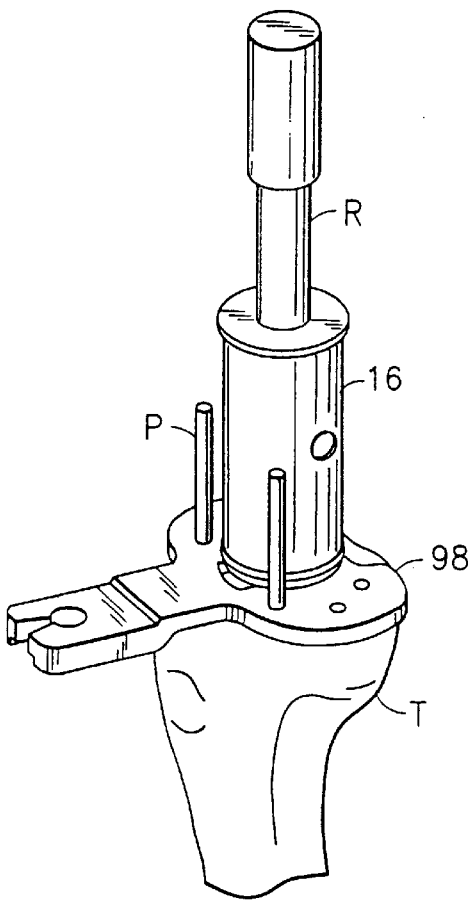

As an additional benefit of the invention, the reamer sleeve 16 and the reamer bushings 18A, 18B can be used in conjunction with a tibial template 98 for preparing a reamed channel into the resected surface of the tibia T. The tibial template 98 is preferably generally formed as the tibial template disclosed in U.S. Pat. No. 5,735,904, but with a plurality of bone pin apertures 99 extending therethrough and an aperture 100 that is identically formed to the guide aperture 36 of the anterior-posterior femoral resection guide 12 to cooperatively receive the reamer sleeve 16 in a bayonet locking fashion. In one embodiment, one of the recesses 46 may be extended radially to define an open mouth 46A in the tibial template 98. In this manner, the reamer sleeve 16 can be readily attached and detached to the aperture 100. In use, as shown in FIGS. 13–15, the tibial template 98 is fixed to the resected surface of the tibia T with the bone pins P extending through the bone pin apertures 99, the reamer sleeve 16 is mounted to the aperture 100, and an appropriate sized reamer bushing 18A, 18B is selected for guiding a reaming tool R. It should be noted, that the tibial template 98 preferably has a sufficiently large plano configuration to rest upon the hard cortical bone about the perimeter of the resected surface of the tibia T in use, rather than the soft spongy inner portions of the tibia T.

It should be noted that although the discussion set forth above is limited to the preparation of a natural knee joint for receiving a prosthetic joint, the subject invention can be used to prepare natural bone condylar joints other than the knee joint, including, for example, an elbow joint, a finger joint, and a toe joint.

Although preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A set of instruments for the preparation of a natural bone in a condylar joint for receiving a prosthetic component, said instruments for guiding channel forming tools in forming a channel in the natural bone extending from a distal end thereof, said instruments used for guiding a cutting instrument in resecting both anterior and posterior portions of the natural bone, said set of instruments comprising:

a resection guide having a generally rectangular body including spaced-apart, opposed planar anterior and planar posterior resection guide surfaces for guiding the cutting instrument, spaced-apart, generally opposed front and rear surfaces extending between said anterior and posterior resection guide surfaces, and a guide aperture extending through said rear surface and towards said front surface; and a set of collets formed to be detachably mounted to said guide aperture, each said collet defining an inner passage shaped and dimensioned to allow passage therethrough of at least one of the channel forming tools, said set of collets including a generally tubular reamer sleeve and a plurality of reamer bushings, each said reamer bushing being formed to telescopically slide into said reamer sleeve.

2. A set of instruments as in claim 1, wherein each said reamer bushing has a generally tubular shape and an hollow inner passage, and wherein each said reamer bushing is formed with a different size inner passage.

3. A set of instruments as in claim 1, wherein said body of said resection guide is formed with at least one handle.

4. A set of instruments as in claim 1, wherein the condylar joint is a knee joint, and, wherein, the natural bone is a femur.

5. A set of instruments for the preparation of a natural bone in a condylar joint for receiving a prosthetic component, said instruments for guiding channel forming tools in forming a channel in the natural bone extending from a distal end thereof, said instruments used for guiding a cutting instrument in resecting both anterior and posterior portions of the natural bone, said set of instruments comprising:

a resection guide having a generally rectangular body including spaced-apart, opposed planar anterior and planar posterior resection guide surfaces for guiding the cutting instrument, spaced-apart, generally opposed front and rear surfaces extending between said anterior and posterior resection guide surfaces, and a guide aperture extending through said rear surface and towards said front surface;

a set of collets formed to be detachably mounted to said guide aperture, each said collet defining an inner passage shaped and dimensioned to allow passage therethrough of at least one of the channel forming tools; and wherein said guide aperture and at least one said collet are formed with cooperative bayonet locking elements for achieving detachable mounting therebetween.

6. A set of instruments both for the preparation of a natural femur for receiving a prosthetic component and for the preparation of a natural tibia for receiving a prosthetic component, said instruments for guiding channel forming tools in both forming a channel in the femur extending from a distal end thereof and in forming a channel in the tibia extending from a resected surface thereof, said instruments also used for guiding a cutting instrument in resecting both anterior and posterior portions of the femur, said set of instruments comprising:

an anterior-posterior femoral resection guide having a generally rectangular body including spaced-apart, opposed planar anterior and planar posterior resection guide surfaces for guiding the cutting instrument, spaced-apart, generally opposed front and rear surfaces extending between said anterior and posterior resection guide surfaces, and a guide aperture extending through said rear surface and towards said front surface;

a tibial template having a generally planar resting surface for resting upon the resected surface of the tibia, and a tibial guide aperture; and a set of collets formed to be detachably mounted to both said guide aperture and said tibial guide aperture, each said collet defining an inner passage shaped and dimensioned to allow passage therethrough of at least one of the channel forming tools.

7. A set of instruments as in claim 6, wherein said set of collets includes a generally tubular reamer sleeve and a plurality of reamer bushings, each said reamer bushing being formed to telescopically slide into said reamer sleeve.

8. A set of instruments as in claim 7, wherein each said reamer bushing has a generally tubular shape and an hollow inner passage, and wherein each said reamer bushing is formed with a different size inner passage.

9. A set of instruments as in claim 6, wherein said guide aperture and at least one said collet are formed with cooperative bayonet locking elements for achieving detachable mounting therebetween.

10. A set of instruments as in claim 9, wherein said tibial guide aperture and at least one said collet are formed with cooperative bayonet locking elements for achieving detachable mounting therebetween.

11. A set of instruments as in claim 6, wherein said body of said anterior-posterior femoral resection guide is formed with at least one handle.

* * * * *